Figure 1:
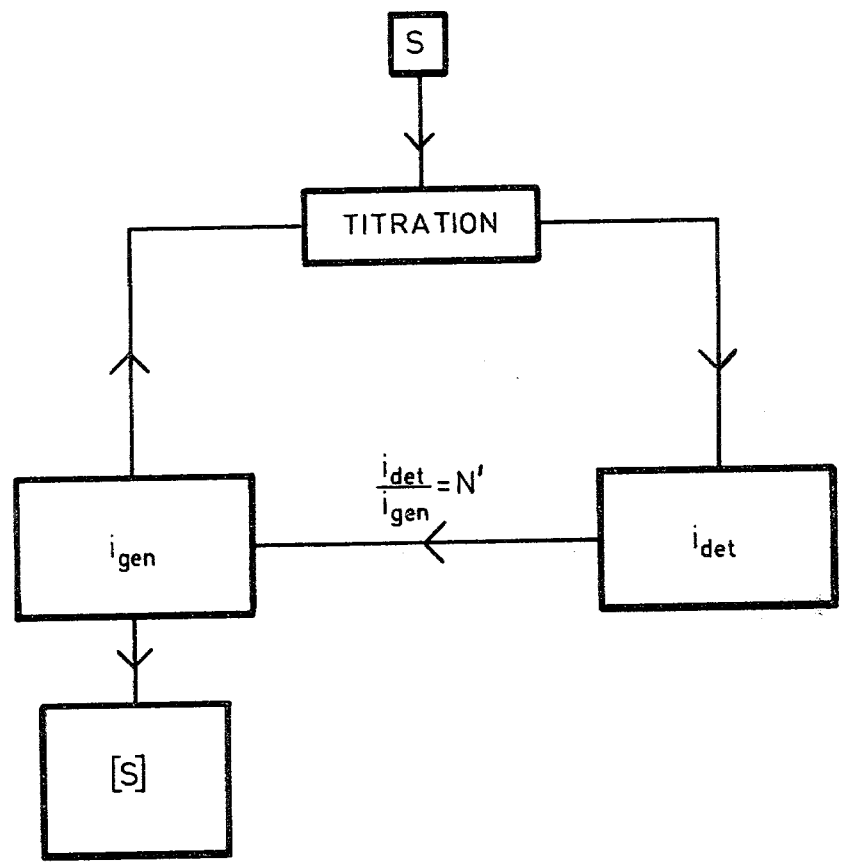

United States Patent [19]

Albery et al.

[11] 4,312,715
[45] Jan. 26, 1982

[54] METHOD AND AN APPARATUS FOR ELECTROCHEMICAL ANALYSIS

[76] Inventors: John Albery, Flat 8, Queens Garden, London W2 3AS; Peter Wood, 3 Manor Pl., Holy Well, Oxford, both of England

[21] Appl. No.: 220,285

[22] Filed: Dec. 29, 1980

Related U.S. Application Data

[63] Continuation of Ser. No. 123,041, Feb. 20, 1980, abandoned.

[30] Foreign Application Priority Data

Feb. 26, 1979 [SE] Sweden .................................. 7901682

[51] Int. Cl.$^3$ ............................................. G01N 27/44
[52] U.S. Cl. .................................. 204/1 T; 23/230 R; 204/195 T; 422/75; 422/76
[58] Field of Search .................. 204/195 T, 1 M, 1 B; 422/75, 76, 77; 23/230 R

[56] References Cited

U.S. PATENT DOCUMENTS 3,338,812  8/1967  Dworak et al. ................. 204/195 T Primary Examiner—G. L. Kaplan
Attorney, Agent, or Firm—Fred Philpitt

[57] ABSTRACT

An autotitration method for electrochemically determining the concentration of a substance (S) contained in a fluid, which is arranged to flow past a generator electrode (2) and downstream thereof a detector electrode (3), said substance being capable of reacting with a species which is generated electrochemically at the generator electrode, the non-reacted portion of said species being detected electrochemically at the detector electrode. According to the invention the generator electrode current ($i_{gen.}$) is controlled in response to the ratio between the detector electrode current ($i_{det.}$) and the generator electrode current so as to maintain said ratio ($i_{det.}/i_{gen.}$ or $i_{gen.}/i_{det.}$) at a pre-determined value (N'). Either of said currents ($i_{gen.}$ or $i_{det.}$), which is a function of the concentration of the substance to be determined, is then measured.

The invention further discloses a device for carrying out this autotitration method.

9 Claims, 13 Drawing Figures

METHOD AND AN APPARATUS FOR ELECTROCHEMICAL ANALYSIS

This is a continuation of application Ser. No. 123,041, filed Feb. 20, 1980, and now abandoned.

The present invention relates to a method and an apparatus for electrochemically determining the concentration of a substance contained in a fluid. More particularly, the invention relates to an improved titration type of electrochemical analysis, wherein a species capable of reacting with the substance to be analysed is generated at a generator electrode, the non-reacted portion of said species being detected at a detector electrode.

It is known that many substances are capable of reacting with certain electrochemically active species such as halogens, bromine being a typical example. This type of reaction has been used as a means for determining the concentration of the substance with which the electroactive species reacts. In the so-called diffusion layer titration technique the electroactive species is generated in situ at a generator electrode. The generated species immediately reacts with the substance to be analysed and the amount of non-reacted species is determined at a detector electrode. Titration curves are taken by increasing the generator current linearly with time, measuring the current changes observed at the detector electrode, plotting the titration curves (generator current vs. detector current) on an X-Y chart recorder, and deriving the concentration of the substance.

This titration technique has several obvious disadvantages. For example, it is very slow, the time required for performing one single determination being at least 60 seconds and normally 5 to 10 minutes. An important limitation is also the one shot nature of the determination—the test solution must be removed and replaced for the next determination. Thus, the technique cannot be used for continuous analysis of a sample fluid. The technique also requires the use of an expensive X-Y recorder.

The present invention aims at eliminating or reducing these and other problems of the above described titration technique, and to this end there is proposed an autotitration apparatus and method, which are characterized by the features indicated in the appended claims.

The invention is based on the discovery that, in the above discussed diffusion layer titration technique, the current of the generator electrode or the current of the detector electrode becomes a function of the concentration of the tested substance when the ratio of the detector electrode current to the generator electrode current is kept at a constant value. The basic feature of the invention is thus to control the generator electrode current (generating current, $i_{gen.}$) in response to the detector electrode current (detecting current, $i_{det.}$) in a manner such that the ratio of $i_{det.}$ to $i_{gen.}$ is maintained at a pre-determined value, and to measure either of said currents ($i_{gen.}$ or $i_{det.}$), which is a function of the concentration of the substance to be determined. By measuring either of said currents it is thus possible to get immediate information about the concentration of the substance in question.

The method according to the invention can be used for the quantitative analysis of any substance, which is capable of reacting with an electroactive species as defined above. Amino acids, peptides, proteins, many hormones and drugs, and the like can be mentioned as non-limiting examples of such substances. The method can be carried out using any kind of electroactive species, which is capable of performing the above-mentioned functions, viz. to be produced in situ at the generator electrode, to react the substance to be determined, and to be detected electrochemically at the detector electrode. These reactions can be illustrated schematically as follows:

Generator electrode: $C \pm ne—B$
Intermediate area: $S+B—SB$
Detector electrode: $B' \mp ne—C'$ C represents a substance (including ions) from which the species B is produced by the electrode reaction at the generator electrode, S represents the substance to be determined, and C' is the same substance as C or represents a different substance (including ions) formed from B' at the detector electrode. B' is the amount of B that has not reacted with S.

The halogens chlorine, bromine and iodine, as well as the corresponding anions from their hypohalous acids, i.e. hypochlorite, hypobromite and hypoiodite, can be mentioned as non-limiting examples of suitable species having the desired electrochemical and chemical properties.

The method according to the invention can be carried out using varying types of detector and generator electrodes, for example the same types of electrodes as have earlier been used for preparing titration curves in the diffusion layer tritration technique referred to above. One example of a suitable electrode assembly is the so-called rotating ring-disc electrode (RRDE), comprising a generator electrode designed as a central disc (or inner ring), and a detector electrode designed as a concentric outer ring, a flow of the fluid containing the substance to be analysed being obtained by rotation of the ring-disc electrode assembly. Another example of a suitable generator/detector assembly is the so-called tubular double electrode (TDE), in which the two electrodes are located in a channel through which the fluid containing the substance to be analyzed is arranged to flow, the detector electrode being located downstream of the generator electrode. Still another example of suitable electrode design is a modification, which can be regarded as a combination of the RRDE and TDE electrodes. In this variant—which might be called a "double wall-jet electrode"—a ring-disc type electrode is located in an outlet channel with the disc (generator) part arranged opposite to an inlet for the fluid to be analyzed, so that the fluid stream hits the generator electrode essentially perpendicularly to the outlet channel, whereas the ring (detector) electrode is arranged with one portion in each of two downstream branches of said channel, thus serving as outlets for said fluid. The three main types of electrode assemblies mentioned above will be described in more detail below, but it is to be understood that the invention is not limited to these electrode types, but any electrode assembly offering a suitable (especially laminar) flow pattern from a generator electrode to a detector electrode can be used for the purposes of the invention.

A most interesting feature of the invention is that it makes it possible to continuously and instantaneously analyse a flowing fluid by means of the above-mentioned titration technique. As a result, this technique can be used in a great variety of analysis applications, wherein the prior art "batch-wise" and time-consuming procedures have been impossible to use. For example, it is impossible to use the prior art techniques for continuous detection in liquid chromatography, whereas the method according to the invention is very well suited for this purpose. Furthermore, it has been found that the autotitration method and apparatus according to the invention can be used not only for quantitative analysis, but also as an aid for the identification of the above-mentioned types of substances, in particular proteins and other substances containing amino groups. It has thus been found that valuable information about the substance to be analysed can be obtained by comparing the results of two tests run at acidic pH and alkaline pH respectively. This technique is based on the fact that certain of the functional groups of the tested substance (such as amino groups), which react with the above-mentioned electroactive species at alkaline pH, fail to react with said species at acidic pH (e.g. because of protonization of amino groups). It has, according to the invention, been found that the ratio of the current readings of these two measurements, i.e. at acidic pH and alkaline pH respectively, is characteristic for each individual substance. In fact, said ratio is in many instances sufficient for determining which substance (e.g. a protein) is present in a sample fluid (e.g. the eluate from a column chromatographic separation). As in e.g. UV-measurements there is a specific proportionality constant between the (current) readings and the concentration. This proportionality constant is specific for each individual substance and is pH dependent. Knowing the concentration of the substance the current reading at acidic pH, divided by the concentration, may be plotted in a diagram against the current reading at alkaline pH, divided by the concentration. The position of this point in the diagram has been found to be unique for a particular substance. If the concentration is unknown the same result can be obtained by dividing the current reading by e.g. the absorbance reading of a simultaneous UV-measurement.

Figure 2:
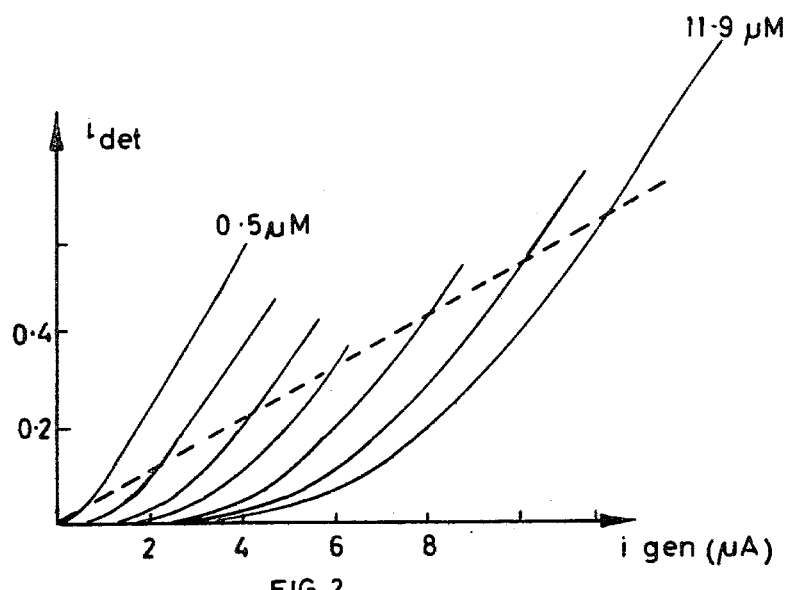
Figure 8:
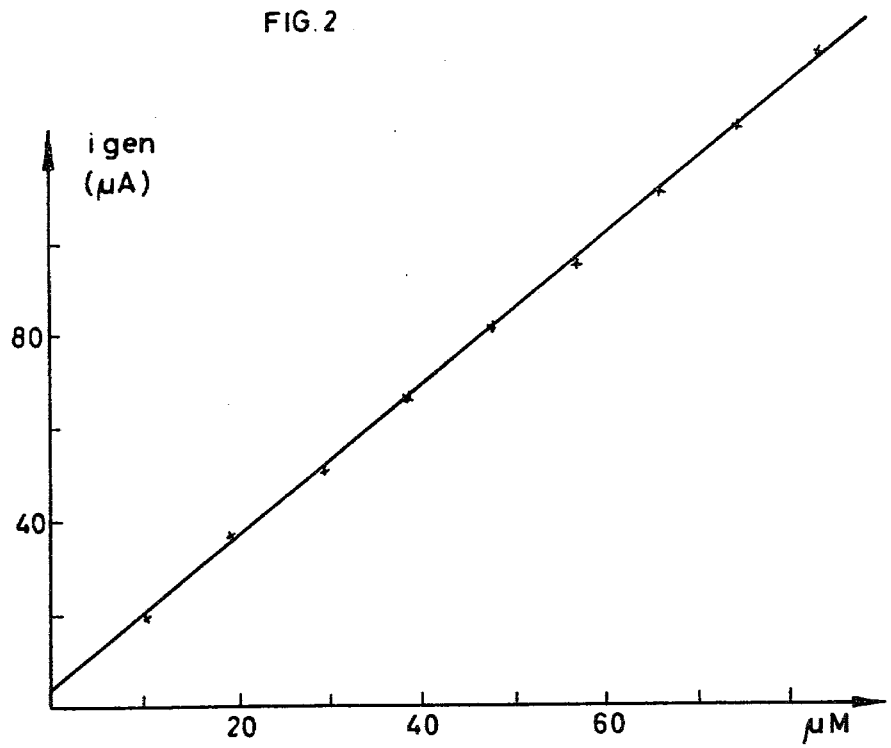
Figure 3:
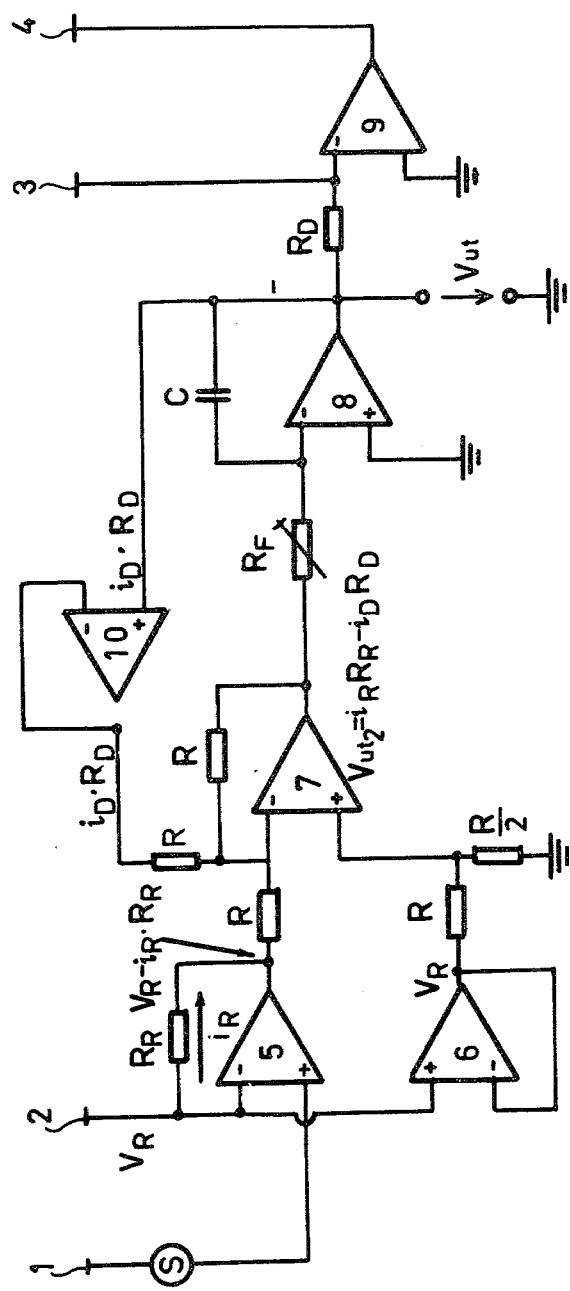
Figure 4A:
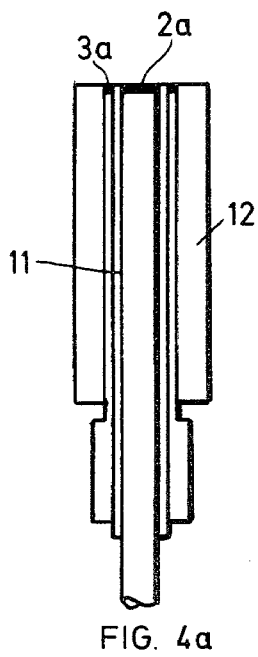
Figure 4B:
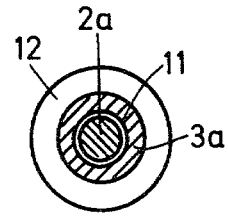
Figure 6:
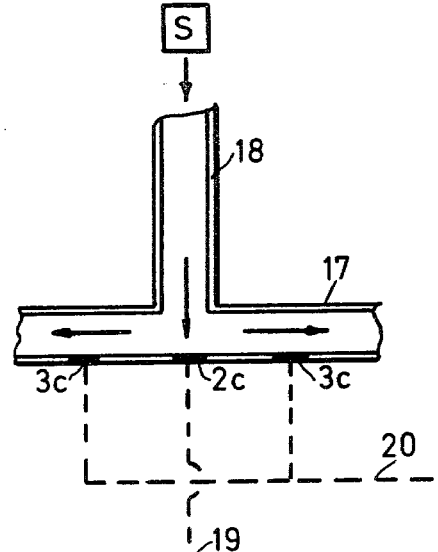
Figure 5:
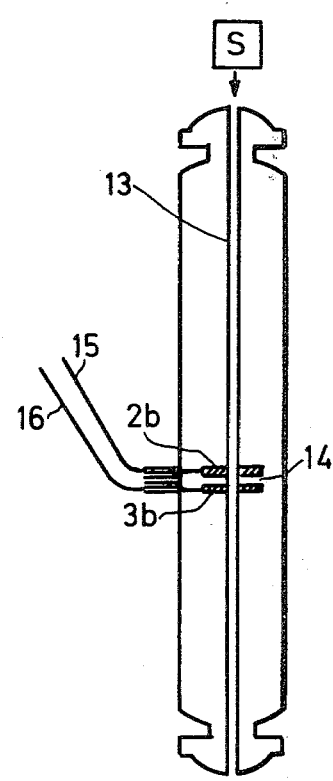
Figure 7:
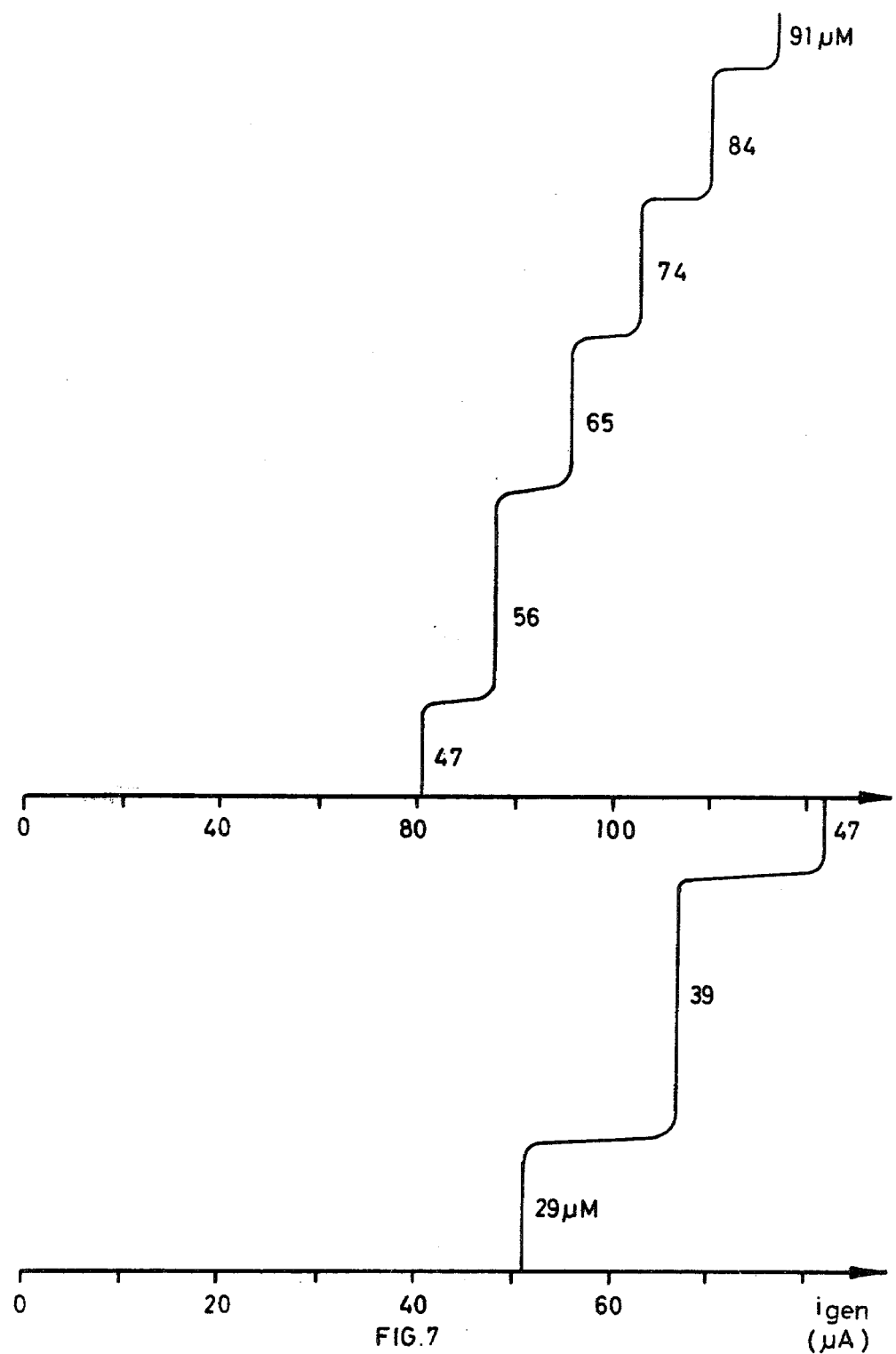
Figure 9:
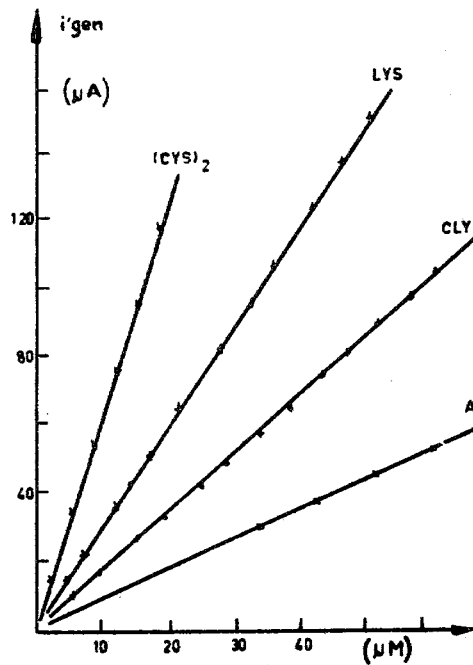
Figure 10:
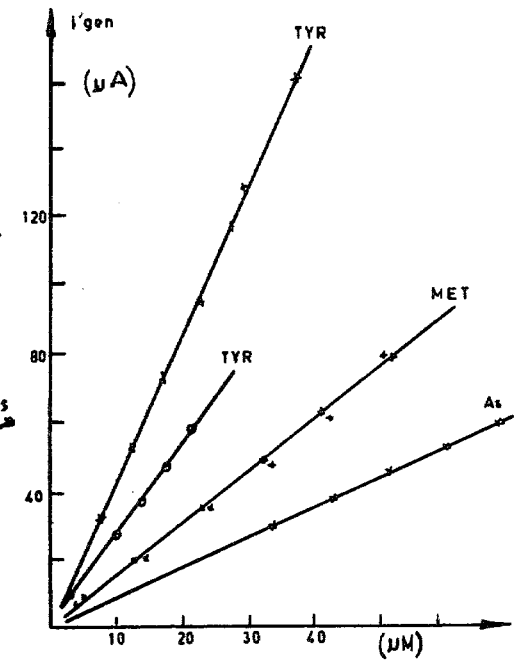
Figure 11:
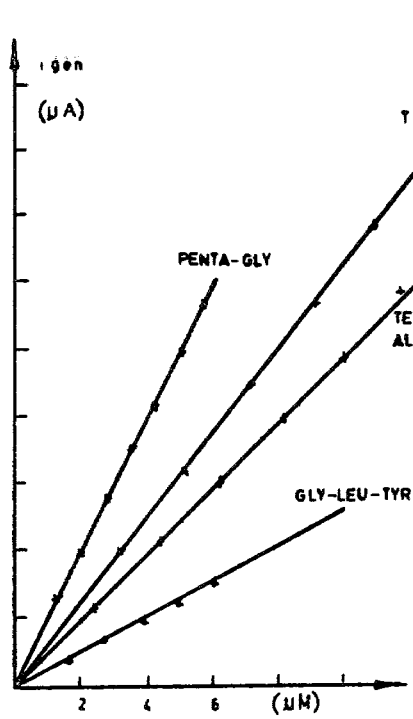

The invention will now be described in more detail with reference to the enclosed drawings, in which FIG. 1 is a block diagram illustrating the method according to the invention, FIG. 2 is a diagram illustrating titration curves for tetra-alanine, FIG. 3 is a circuit diagram illustrating one embodiment of a device for carrying out the method according to the invention, FIGS. 4a and 4b are schematic sectional veiws of one embodiment of a rotating ring disc electrode, which can be used in the method according to the invention, FIG. 5 is a schematic sectional view of one embodiment of a tubular double electrode, which can be used in the method according to the invention, FIG. 6 is a schematic sectional view of a double wall-jet electrode, which can be used in the method according to the invention, FIG. 7 is a time-concentration diagram taken by the method according to the invention for As(III), FIG. 8 is a current-concentration diagram for the test illustrated in FIG. 7, and FIGS. 9 to 12 are diagrams corresponding to FIG. 7 and relating to different substances tested by means of the method according to the invention.

The block diagram of FIG. 1 illustrates the basic principle of the method according to the invention. A test fluid containing the substance S to be analyzed is brought to react with an electrogenerated species at a TITRATION station comprising generator and detector electrodes. The ratio of the detector electrode current to the generator electrode current ($i_{det.}/i_{gen.} = N'$) is monitored continuously, and as soon as the monitored ratio N′ deviates from a predetermined value the generator electrode current $i_{gen.}$ is adjusted so as to maintain the ratio N′ at the pre-determined value. Thus, if the ratio $i_{det.}/i_{gen.}$ should tend to fall below the pre-determined value the generator electrode current is decreased, and vice versa.

The concentration of the substance S in the tested fluid is determined by measuring the generator electrode current $i_{gen.}$, which is a function of the concentration of the substance S. Of course, the same is true for the detector electrode current $i_{det.}$. As the monitored current is a function of the desired concentration the current reading can easily be transformed into concentration values. If the value of N′ is selected so as to intersect the corresponding titration curves (compare FIG. 2 which illustrates titration curves for tetra-alanine) in the linear regions thereof, then $i_{gen.}$ (and $i_{det.}$) becomes directly proportional to the desired concentration. Although this may be preferred for practical reasons, the invention is not limited to this area, but any other value of N′ for which the N′ line intersects the titration curves can be used. It may, as a non-limiting example only, be mentioned that the N′ value may be from 0.02 to 0.20, e.g. from 0.04 to 0.10. When the N′ line intersects the non-linear portions of the titration curves, then the reading unit should be provided with suitable means to compensate for the non-linear current-/concentration relationship when transforming the current readings into concentration readings. This can be achieved by means of recording equipment well known to a person skilled in the art.

FIG. 3 illustrates one embodiment of an electronic circuit, which can be used for carrying out the method according to the invention as disclosed above. This electronic circuit comprises a reference electrode 1, a detector electrode 2, a generator electrode 3, a counter electrode 4, and operational amplifier units 5–10. The detector electrode 2 is connected, on the one hand, to the inverting input a first amplifier 5 having a negative feedback via a resistance $R_R$, and on the other hand to the non-inverting input of a second amplifier 6 having a negative feedback. The reference electrode 1 (e.g. a saturated calomel electrode) is connected to the non-inverting input of the amplifier 5. The outputs of the amplifiers 5 and 6 are connected to the inverting and non-inverting inputs respectively of a third amplifier 7 via an input resistance R, the non-inverting input also being earthed through a resistance R/2. The amplifier 7 has a negative feedback via a resistance R, and the output is connected to the inverting input of the amplifier 8 via a variable resistance $R_F$. The amplifier 8 has a negative feedback through a condensor C and an earthed non-inverting input. On the output side the amplifier 8 is fed back to the inverting input of the amplifier 7 via another amplifier 10, which has a negative feed-back and a resistance R. The output of the amplifier 8 is further via a resistance $R_D$ and together with a generator electrode 3 connected to the inverting input of the amplifier 9. The non-inverting input of the amplifier 9 is earthed and the output is connected to the counter electrode 4. In the above circuit the amplifier unit 5 functions as a current-to-voltage convertor, the amplifier units 6 and 10 as potential followers, the amplifier 7 as a summer/subtractor, the amplifier 8 as an integrator, and the amplifier 9 as a galvanostat.

In operation the above described electronic circuit balances the current $i_{det.}$ of the detector electrode 2 and the current $i_{gen.}$ of the generator electrode 3, so that the ratio $i_{det.}/i_{gen.}$ is maintained at the pre-determined constant value $N'$. This is achieved by sensing and comparing the voltage drops over the known resistances $R_R$ and $R_D$. If $R_D$ and $R_R$ are chosen so that $R_D/R_R = N'$, then $i_{det.} \cdot R_R = i_{gen.} \cdot R_D$ when $i_{det.}/i_{gen.} = N'$.

The amplifier 5 holds the detector electrode 2 at a suitable potential $V_R$, and the amplifiers 5 and 6 feed the detector electrode current $i_{det.}$ through the amplifier 7. The latter adds the output voltage of the amplifier 5, $V_R - i_{det.} \cdot R_R$, and the output voltage of the amplifier 10, $i_{gen.} \cdot R_D$, and subtracts the output voltage $V_R$ of the amplifier 6. The output signal obtained from the amplifier 7 is thus $V'_{out} = i_{det.} \cdot R_R - i_{gen.} \cdot R_D$. This error signal is delayed in the amplifier 8 depending on the value of the resistance $R_F$ to compensate for the delay in the electrode system between the generator and the detector electrodes. The produced output signal $i_{gen.} \cdot R_D$ controls the current $i_{gen.}$ of the generator electrode 3 via the amplifier 9, and it is also fed back to the amplifier 7. When there is unbalance in the circuit, i.e. when $i_{det.}/i_{gen.} = N'$ then the voltage between the output of the amplifier 8 and earth, $V_{out}$, is changed until $i_{det.} \cdot R_R - i_{gen.} \cdot R_E = 0$. The voltage value obtained is held by the amplifier 8, and $V_{out}$ is then a measure of $i_{gen.}$ ($i_{det.}$) since $V_{out} = i_{gen.} \cdot R_D$.

FIGS. 4 to 6 illustrate three examples of generator/detector electrode assemblies which can be used in the method and the apparatus according to the invention. FIGS. 4a and 4b illustrate an RRDE electrode comprising a central disc-like generator electrode 2a and an outer, annular detector electrode 3a. The ring electrode 3a is separated from the disc electrode 2a by means of an insulating annulus 11. In the illustrated embodiment the electrode assembly is surrounded by a suitable outer covering 12, and it also has appropriate means for bringing the electrode assembly into rotation, thereby forcing the sample fluid to flow from the generator electrode 2a to the detector electrode 3a. The electrode asembly is, of course, provided with suitable means for electrically connecting the electrodes 2a and 3a to the electronic circuit illustrated in FIG. 3 or to a similar device. This type of electrode is especially suitable for making batch-wise measurements.

The TDE electrode illustrated in FIG. 5 comprises a generator electrode 2b and a detector electrode 3b (both e.g. made of Pt). The two electrodes 2b and 3b both form part of the walls of a channel 13 (such as a capillary tube) through which the fluid to be tested is arranged to flow. The electrodes 2b, 3b are separated by a gap 14, and the detector electrode is located downstream of the generator electrode. The electrodes are connected to suitable wiring 15, 16 for connection to the apparatus illustrated in FIG. 3 or to a similar device. The TDE electrode assembly is very well suited for continuously monitoring the concentration of substances contained in a continuously flowing fluid such as the eluate from a chromatographic separation process, part of said flow preferably being continuously introduced into the channel 13.

In the variant illustrated in FIG. 6 the detector/generator electrode assembly is located in a channel 17, and as in the TDE electrode of FIG. 5 the electrodes preferably form part of the walls of said channel. The fluid containing the substance S to be analyzed is introduced into an inlet channel 18 opening into the channel 17 essentially perpendicularly thereto, the channels 17 and 18 thus forming a T-joint. The generator electrode 2c is located opposite to the channel 18 so that the fluid hits the electrode surface 2c when entering the channel 17. The fluid stream is then forced to flow in both directions through the channel 18, passing over the electrode surfaces of the detector electrodes 3c. Suitable electrical connectors 19 and 20 connect the electrodes with the electronic circuit illustrated in FIG. 3 or with a similar device. With regard to the operation of this type of electrode assembly the same can be called a "double wall-jet electrode". As an alternative one outlet branch of the channel 17 can be eliminated (together with the corresponding detector electrode part, e.g. 3c), thus forming an L-shaped joint between the channels 17 and 18.

The autotitrator circuit illustrated in FIG. 3 and the autotitration technique according to the invention were tested by titrating As(III) with bromine (bromination) by means of an RRDE electrode according to FIG. 4. 100 ml of a solution consisting of 0.5 M $H_2SO_4$ (p.a.) and $10^{-3}$ M of KBr (p.a. in double distilled water) was poured into an electrochemical cell. The RRDE electrode was assembled and inserted into the cell and rotated at 20 Hz. The electronic circuit of FIG. 3, with $N'$ adjusted to 0.06, was connected to the disc (generator) electrode 2a, to the ring (detector) electrode 3a (FIG. 4), and to the reference electrode 1 and the counter electrode 4 (FIG. 3). A $10^{-3}$ M solution of As(III) was prepared by dissolving arsenic trioxide in double distilled water. 1 ml thereof was added to the 100 ml solution in the electrochemical cell. The autotitrator circuit was switched on, and it stabilized after approximately 5 seconds at a disc current $i_{gen.}$ of 19.6 $\mu$A. A second 1 ml aliquot of the As(III) solution was added to the cell, resulting in an increase of the disc current to 36.5 $\mu$A. A t-Y chart recorder was then used to continuously monitor the disc current as additional 1 ml aliquots of the As(III) solution were added to the cell. The recorded results obtained are illustrated in FIG. 7.

The As(III) concentrations in the cell were calculated and then plotted (X-axis) against the disc currents $i_{gen.}$ (Y-axis), and the resulting diagram is illustrated in FIG. 8. The concentration-disc current relation obtained is a straight line, which shows that the autotitrator circuit controls the generator (disc) current, so that said current is directly proportional to the As(III) concentration.

Similar results were obtained when repeating the experiment using the TDE electrode of FIG. 5.

Figure 12:
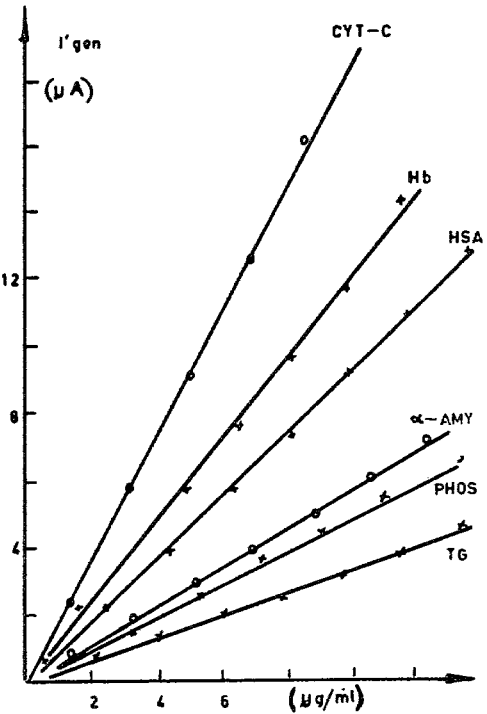

In the same way corresponding linear current-concentration relationships were obtained for the amino acids cystine, lysine and glycine (FIG. 9), tyrosine, tryptophan and methionine (FIG. 10); the peptides penta-Gly, tri-Tyr, tetra-Ala and Gly-Leu-Tyr (FIG. 11) and the proteins cytochrome C, haemoglobin, human serum albumin (HSA), $\alpha$amylase, phosvitin, and thyroglobulin (FIG. 12).

The above described autotitration method and apparatus were used for identifying the proteins haemoglobin (Hb), cytochrome C (CytC), human serum albumine (HSA), bovine serum albumine (BSA), thyroglobulin (T-Glob), and phosvitin (Phos) by bromination at alkaline pH ($\sim$9.2) and at acidic pH ($\sim$5) respectively. (KBr was used for producing the electrogenerated species). For each protein the current readings were adjusted to the dimension $\mu$A/$\mu$g protein/ml, (i.e. by dividing the current readings by the concentration) and the adjusted values were plotted in a diagram (acidic vs. alkaline values), preferably after having been normalized to the values for HSA (HSA=1:1). The plotted relationship between the alkaline and acidic readings turned out to give most valuable information about the identity of the proteins—each individual protein falls within a well-defined area of the diagram, which thus can be used as a standard. By making two measurements of an unknown protein (i.e. at alkaline and acidic pH), adjusting the readings as described, and comparing the result with said standard, it may thus be possible to identify the protein. If the concentration is unknown the same procedure can be used and equivalent results be obtained by dividing the current readings by the absorbance readings from a simultaneous UV-measurement (obtaining results of e.g. the dimension $\mu A/a.\lambda$). If there are still doubts concerning the identity of the protein, a conventional UV-test (e.g. at 254 nm) can be used as a complement, in particular by relating—similarly as described above—the UV-reading either to the autotitration reading at acidic or alkaline pH or to the indicated ratio therebetween.

What we claim is:

1. An autotitration method for electrochemically determining the concentration of a substance contained in a fluid that is arranged to flow past a generator electrode and downstream thereof a detector electrode, said substance being capable of reacting with a species which is generated electrochemically at the generator electrode, the non-reacted portion of said species being detected electrochemically at the detector electrode, comprising the steps of
   (a) controlling the generator electrode current in response to the ratio between the detector electrode current and the generator electrode current so as to maintain said ratio at a constant value,
   (b) measuring either of said currents which is a function of the concentration of the substance to be determined.

2. The method of claim 1 wherein said predetermined ratio is selected such that, in a corresponding titration diagram for the substance to be determined, the straight line corresponding to said ratio intersects the titration curves at or close to the point where the titration curves become linear.

3. The method of claim 1 wherein said predetermined ratio is selected such that the straight line corresponding to said ratio intersects the corresponding titration curves in the linear portion thereof.

4. The method of claim 1 wherein said electrochemically generated species is chlorine, bromine, or iodine or the corresponding anions from their hypohalous acids.

5. The method of claim 1 wherein the measurement of the generator electrode current is delayed in proportion to the time required for the fluid to pass from the generator electrode to the detector electrode.

6. The method of claim 1 wherein said fluid is arranged to pass the electrode surfaces in an essentially laminar flow pattern.

7. A device for electrochemically determining the concentration of a substance contained in a fluid, said device comprising in combination:
   (a) a generator electrode adapted to contact said fluid and arranged to electrochemically generate a species capable of reacting with said substance,
   (b) a detector electrode adapted to contact said fluid and arranged to detect said species electrochemically,
   (c) means for establishing a flow of said fluid from said generator electrode to said detector electrode,
   (d) means for determining the ratio between the detector electrode current and the generator electrode current and controlling the generator electrode current such that said ratio is kept at a constant value, and
   (e) means for indicating either of the detector electrode current and the generator electrode current.

8. The device of claim 7 comprising an electronic comparison circuit arranged to compare the detector electrode current with the generator electrode current and further comprising an electronic delay circuit arranged to delay the signal of the generator electrode current in proportion to the time required for said fluid to flow from the generator electrode to the detector electrode.

9. The device of claim 7, comprising an electrode assembly selected from the group consisting of
   (a) a tubular double electrode having two spaced apart electrodes adapted to being arranged in a channel for said fluid, the electrode serving as the detector electrode and being located downstream of the electrode serving as the generator electrode,
   (b) a rotatable ring-disc electrode having a central disc electrode serving as the generator electrode, and an outer concentric annular electrode serving as the detector electrode, and
   (c) a wall-jet electrode having two electrodes arranged in a channel for said fluid, said channel having a fluid inlet located opposite to the electrode serving as the generator electrode and so arranged that the fluid stream from the inlet will hit the generator electrode essentially perpendicularly to the electrode surface, the detector electrode being located downstream of the generator electrode, and each of said electrodes preferably forming part of the wall of said channel.

* * * * *